United States Patent
Abitbol et al.

(10) Patent No.: US 9,462,939 B2
(45) Date of Patent: Oct. 11, 2016

(54) OBJECTIVE PHOROPTER SYSTEM

(71) Applicant: VISIONIX LTD., Jerusalem (IL)

(72) Inventors: Marc Abitbol, Jerusalem (IL); Ran Yam, Jerusalem (IL); Haggai Herman, Givat Shmuel (IL); Ian Melnick, Jerusalem (IL)

(73) Assignee: VISIONIX LTD., Jerusalem (IL)

( * ) Notice: Subject to any disclaimer, the term of this patent is extended or adjusted under 35 U.S.C. 154(b) by 0 days.

(21) Appl. No.: 14/390,794

(22) PCT Filed: Apr. 4, 2013

(86) PCT No.: PCT/IL2013/000037
§ 371 (c)(1),
(2) Date: Oct. 6, 2014

(87) PCT Pub. No.: WO2013/150513
PCT Pub. Date: Oct. 10, 2013

(65) Prior Publication Data
US 2015/0042957 A1    Feb. 12, 2015

Related U.S. Application Data

(60) Provisional application No. 61/686,426, filed on Apr. 5, 2012.

(51) Int. Cl.
*A61B 3/10* (2006.01)
*A61B 3/02* (2006.01)
*A61B 3/028* (2006.01)

(52) U.S. Cl.
CPC .......... *A61B 3/0285* (2013.01); *A61B 3/1015* (2013.01)

(58) Field of Classification Search
CPC .. A61B 3/1015; A61B 3/0285; A61B 3/103; A61B 3/028; A61B 3/032; A61B 3/04; A61B 3/0075; A61B 3/02

USPC .................................................. 351/222–244
See application file for complete search history.

(56) References Cited

U.S. PATENT DOCUMENTS

| | | | |
|---|---|---|---|
| 6,736,509 B2 | 5/2004 | Martino | |
| 7,357,509 B2 | 4/2008 | Williams | |

(Continued)

FOREIGN PATENT DOCUMENTS

| | | | |
|---|---|---|---|
| IL | WO 2009/024981 A2 | * | 2/2009 |
| JP | H08-154896 | | 6/1996 |

(Continued)

OTHER PUBLICATIONS

International Search Report and Written Opinion in PCT application No. PCT/IL2013/000037 published on Jul. 21, 2013.

(Continued)

*Primary Examiner* — Mahidere Sahle
(74) *Attorney, Agent, or Firm* — Daniel J. Swirsky; AlphaPatent Associates Ltd.

(57) ABSTRACT

Systems for performing combined phoropter and refractive measurements to ascertain the aberrations present in the eye of a subject. The systems use a pair of phoropter wheel assemblies, one for each eye, each assembly comprising a number of lens wheels incorporating the series of lenses and wedges required to compensate for a range of refractive vision aberrations. The vision of each eye is corrected by a combination of a subjective phoropter measurement, iteratively performed with an objective wavefront analysis measurement to determine the residual aberrations existing after the initial phoropter correction. The system is able to automatically align the axes of each wavefront analyzer with is corresponding eye, by means of centering the pupil image in the wavefront analyzer camera, and to determine the pupil distance. By changing the focusing point on the wavefront analyzer of the light reflected from the eye, the corneal profile can be measured.

14 Claims, 7 Drawing Sheets

(56) References Cited

U.S. PATENT DOCUMENTS

| | | |
|---|---|---|
| 2003/0081174 A1* | 5/2003 | Ross .................. A61B 3/1015 351/212 |
| 2004/0100619 A1 | 5/2004 | Olivier |
| 2008/0018855 A1 | 1/2008 | Larichev |
| 2009/0073384 A1 | 3/2009 | Warden |
| 2010/0110379 A1* | 5/2010 | Zhou ........................ G01J 9/00 351/211 |
| 2011/0228225 A1 | 9/2011 | Liang |

FOREIGN PATENT DOCUMENTS

| | | |
|---|---|---|
| WO | 2005/037090 | 4/2005 |
| WO | 2009/024981 | 2/2009 |

OTHER PUBLICATIONS

Extended European Search Report in EP application No. 13772990.1 published Dec. 22, 2015.

* cited by examiner

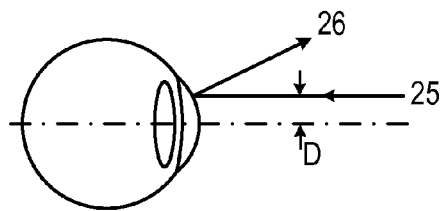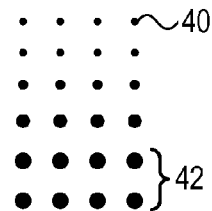
FIG. 2　　　　　　　FIG. 4
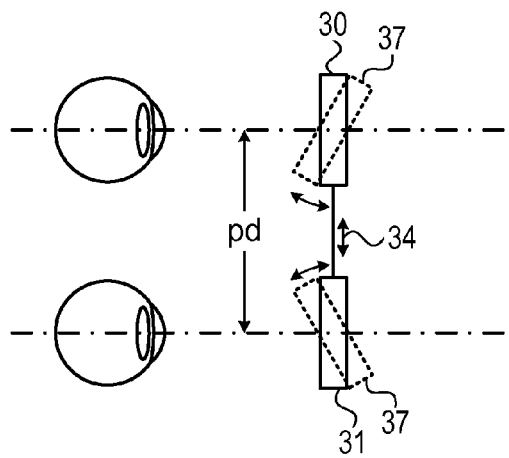
FIG. 3
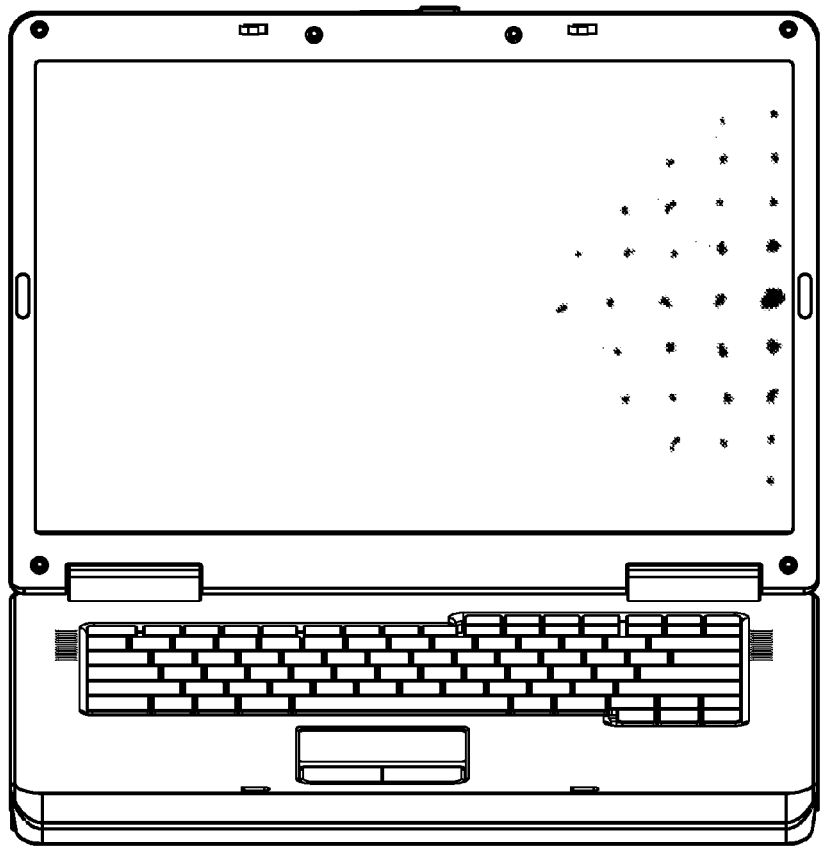
FIG. 5

OBJECTIVE PHOROPTER SYSTEM

CROSS-REFERENCE TO RELATED APPLICATIONS

This application is a U.S. National Phase Application under 35 U.S.C. 371 of International Application No. PCT/IL2013/000037, which has an international filing date of Apr. 4, 2013, and which claims priority from U.S. Provisional Patent Application No. 61/686,426, filed Apr. 5, 2012, the contents of which are incorporated herein by reference in their entirety.

FIELD OF THE INVENTION

The present invention relates to the field of ophthalmic measurement apparatus, especially that combining phoropter measurements and wavefront analysis, such that a phoropter measurement can be performed more objectively.

BACKGROUND OF THE INVENTION

There are two main methods of determining the refractive properties of an eye for the purpose of providing correction lenses. One of those methods is subjective and the other objective. The subjective method is that of the familiar phoropter, in which the subject is asked to view a test plate, while optical elements of different spherical power and different cylindrical correction are inserted in front of the subject's eye under test. The subject provides the optometrist with the subject's view of which lens or lens combination provides the best vision, and the optometrist converges on this best subjective lens prescription.

There are a number of objective methods including that of direct measurement of the aberrations arising in a wavefront emitted from a point of light focused onto the retina of the eye of the subject. The difference between the aberrated wavefront emitted from the eye and a planar undistorted wavefront is measured using a wavefront analysis system, such as that based on a Shack-Hartmann array. The output of such an instrument is a map of the refractive properties across the eye, which can be used to determine the form and strength of spectacle lenses for correction of the aberration measured. A number of instruments have been described in the prior art for performing this wavefront analysis.

There is a certain advantage in a combination instrument involving a phoropter measurement in combination with a wavefront analyzer. Such a combination instrument has been described in International Patent Application Number WO 2005/037090 for "Method and Device for Determining the Residual Defective Vision of a Patient" to Ingo Mueller-Vogt, hereby incorporated by reference in its entirety. However the instrument described therein has a number of disadvantages. The illumination laser source is deflected into the measurement beam path on the imaging side of the phoropter assembly, such that it passes through the phoropter elements on its path towards the subject's eye. In its path through the phoropter elements, part of the incident laser light may be reflected back towards the Shack-Hartmann detection array, and the intensity of this reflected light may be substantially larger than that of the weak reflection from the retina, making measurement of the retinal reflection difficult. Furthermore, the mode of the laser beam may be degraded in its path through the phoropter elements.

There therefore exists a need for a combination optical refraction measurement system which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for performing combined phoropter and refractive measurements to ascertain the aberrations present in the eye of a subject. The systems use a pair of phoropter wheel assemblies, one for each eye, each assembly comprising a number of lens wheels incorporating the series of lenses and wedges required to compensate for a wide range of refractive aberrations in the vision of the eye being tested. The vision of each eye is corrected by a combination of a subjective phoropter measurement, iteratively performed with an objective wavefront analysis measurement to determine the residual aberrations existing after the initial phoropter correction. The wavefront analysis measurement can be performed by any of the known methods, and particularly by the use of a Shack-Hartmann array to analyze the deviation of the retinal reflected wavefront from a planar wave, as is known in the art. The Shack-Hartmann technique will be used throughout this disclosure as an example of a wavefront measurement configuration, though it is to be understood that it is not the only method of wavefront analysis, and is not meant to limit the application thereto.

The major advantage of such an instrument is that the aberration measurement using the wavefront analyzer is performed on a wavefront emitted from an eye that has been approximately corrected by means of the subjective phoropter measurement. Two advantages become apparent. Firstly, a subjective phoropter measurement alone can be difficult to perform accurately, especially for vision defects with significant higher order aberration content, because of the dependence of the measurement on the subject's subjective response. Furthermore, even if the subjective response were accurate, there is great difficulty in optimizing a function (the subject's vision) when three or more variables (the lenses or prisms of the three or more phoropter wheels) need to be changed alternately and iteratively to reach the situation of minimal aberrations, especially in the presence of significant higher order aberrations. In a combination phoropter/wavefront measurement on the other hand, the phoropter measurement does not have to be performed to its ultimate point of accuracy, since any residual aberrations not properly corrected by the initial phoropter setting, can be readily measured by the objective wavefront measurement and added to the phoropter reading to provide a better starting point for another iteration, or for providing a more accurate prescription. Advantageously, the phoropter may be an automated digitally controlled model, such that the objectively measured levels of aberration output from the wavefront analyzer may be input directly to the digital phoropter, and the lenses adjusted therein automatically to reflect the objectively measured aberration levels.

Secondly, after passage through the phoropter, the corrected wavefront is closer to being a planar wavefront, and the residual aberration left for measurement by the wavefront analyzer is small and therefore accurately measurable. Although most wavefront measurement systems incorporate a lens for correction of power of the eye, such that the measurement is generally made on a reasonably corrected eye, the currently proposed combination system has the advantage of additionally providing cylinder correction, providing a much better corrected eye on which the wavefront analysis is performed.

The systems of the present disclosure differ from prior art systems in that either of, or more advantageously, both of the lateral pupil distance adjustment of the two phoropter wheel assemblies and the mutual angular tilt adjustment mechanism of the two phoropter wheel assemblies are part of a control system whose target function depends on the particular measurement being performed with the combination instrument. Commonly, the motion control can be used to ensure that the illuminating beam for the wavefront analysis is maintained at a predetermined small distance from the optical axis of the eye. This ensures that the strong corneal reflections are prevented from entering the wavefront analysis system, where they may drown out the weak signals arising from the reflection from the retina of the illuminating beam. An image processing system operating on the image obtained in the wavefront analysis detector array can be used to provide the feedback signal for controlling the two phoropter adjustment mechanisms.

As an additional feature to reduce the effect of reflections on the ease of performing the wavefront analysis measurement, the illumination laser beam is injected into the optical path between the phoropter assemblies and the subject's eye(s), such that it does not have to traverse the phoropter lenses before entering the eye. This avoids superfluous reflections accruing from the surfaces of the numerous lenses in the path through the phoropter wheels. In order to maintain the required close spacing of the phoropter to the subject's eye, which is required to simulate the correct position of spectacle lenses, a novel thin path length beam splitter is described, which allows a full aperture optical path to be used, yet which has only a short insertion path length in the optical path of the measured beam.

Furthermore, the system is able to perform an automatic pupil distance measurement, using the images of the Shack-Hartmann analyzer to determine when the optical axis of the measurement systems of each eye is centrally aligned relative to the pupil of that eye. The position of the measurement channel of each eye is then adjusted to centralize it on the pupil of that eye. The distance between the two pupil centers can thus be readily and automatically obtained from the known positions of the measurement channels. This is an advantage compared to prior art subjective phoropter systems which have neither measurement, nor automatic adjustment of the pupillary distance, and thus might lead to a deviation from the ideal measurement when the optical path of the phoropter is collinear with the pupils.

Additionally, the pupil diameter itself of each eye can be measured from the Shack Hartmann image, the light reflected from the retina being considered a point source, filling the whole pupil, and then being imaged on the detector. The SH image itself is thus an image of the pupil, from which the diameter can be readily obtained.

Furthermore, unlike prior art wavefront refractometer systems, the focusing assembly of the system is adapted so that it can be adjusted to enable the Shack-Hartmann array to be used in order to measure the corneal profile over the central region of the cornea. This is achieved by firstly moving the measurement axis laterally so that it is accurately collinear with the normal to the cornea at its center point, and by adjusting the focusing position of the SH optics such that they focus the wavefront of the corneal reflection, rather than the retinal reflection wavefront, onto the detector array. This feature enables a limited keratometer measurement to be performed on the same instrument as the refractometric measurements of the aberrations of the eye are performed, by means of simple controlled movements of the measurement channels. The keratometric function is dependent on the spacing between the internal optics of the system. There are many configurations where the retinal reflection will be focused onto the SH detector, but there are specific configurations as well where the corneal reflection is also focused onto the SH detector—in this case the wavefront analyzer can be used as a keratometer. In a different configuration, the corneal reflection can be focused onto the lens array, this minimizing the corneal reflection on the retinal SH image.

The exemplary system described in the present disclosure is therefore capable of implementing four different types of ophthalmic measurements in a single unified instrument, namely a subjective phoropter measurement, a subjective phoropter measurement supported by an associated objective wavefront analysis measurement, a keratometric measurement, and also an automatic pupil distance measurement.

Another important advantage of the exemplary system is the ability to make a binocular measurement while the two eyes are focused on a far or near target, and thus to take into account the binocular affect which is missing on prior art objective measurement devices. In addition to the objective readings of the eyes under binocular condition, the pupillary distance for near vision conditions can also be obtained in this way.

One exemplary implementation involves a system for measuring the refractive properties of the eyes of a subject, the system comprising:

(i) an optical system for directing illuminating beams into the eyes of the subject, (ii) a phoropter comprising separate phoropter assemblies disposed in front of each of the eyes of the subject, such that the vision of each of the eyes of the subject can be subjectively corrected, (iii) at least one of a lateral adjustment mechanism for the phoropter assemblies, or an angular adjustment mechanism for the angular alignment between the phoropter assemblies for each of the eyes of the subject, and (iv) a wavefront analyzer for determining the aberrations of each of the eyes of the subject, the wavefront analyzers being disposed such that light emitted from each of the eyes enters their associated wavefront analyzers after traversing their associated phoropter assemblies, wherein at least one of the phoropter adjustment mechanisms is adapted to enable the illuminating beams to be directed into the eyes of the subject along beam paths not coincident with the optical axes of the eyes of the subject.

In such systems, the lateral adjustment mechanism for the phoropter assemblies may be adapted to measure the subject's pupil distance. In such a case, the lateral adjustment mechanism may be controlled by determining the center of the subject's pupils from an output of the wavefront analyzer. The output image of the wavefront analyzer may be obtained on a detector array, and the intensity distribution of the output image used to control the adjustment mechanisms of the phoropter.

Additional implementations can further comprise illumination sources disposed laterally to the eyes, illuminating the surfaces of the eyes in a dark field mode, such that the wavefront analyzers generate images including arrays of spots from the dark field illumination scattered from the front surfaces of the eyes. The images then depict the position of the pupils of the eyes as regions with substantially less illumination than the rest of the images. The system may then further comprise an image processing system determining the position of the pupils, such that the wavefront analyzers system can be aligned relative to the centers of the pupils without the need for an additional viewing camera.

Such systems may further include focusing assemblies directing light from the eyes into the wavefront analyzers, wherein the focusing assemblies and wavefront analyzers may be disposed on the axis of the eyes, light reflected from the corneal surfaces of the eyes being focused onto the central region of the wavefront analyzers, such that the corneal reflected light does not flood out light reflected from the retinae of the eyes impinging on more peripheral regions of the wavefront analyzer. These focusing assemblies may be such that the light reflected from the retinae of the eyes is directed into the wavefront analyzers in essentially collimated beams, such that the collimated beams cover an appreciable area of the wavefront analyzers peripheral to the central region of the wavefront analyzers.

Still other example implementations of such system involve paths not coincident with the optical axes of the eyes of the subject sufficiently far from the optical axes that corneal reflections into the wavefront analyzers are essentially eliminated while the focused beams still impinge on the retinae of the eyes. In such cases, the illuminating beams should be sufficiently small that the paths are sufficiently far from the optical axes. The size of the illuminating beams may also be increased to enable the increased-size beam to determine the positions of the optical axes of the eyes relative to the axes of the wavefront analyzers.

In any of the above described systems, the wavefront analyzers may be Shack-Hartmann arrays.

Additionally, alternative implementations of such systems for measuring the refractive properties of an eye of a subject may comprise:
(i) an optical system for directing an illuminating beam into an eye of the subject,
(ii) a phoropter disposed in front of the eye of the subject, such that the vision of the eye of the subject can be subjectively corrected, and
(iii) a wavefront analyzer for determining the aberrations of the eye of the subject, the wavefront analyzer being disposed such that light emitted from the eye enters the wavefront analyzer after traversing the phoropter,
wherein the optical system for directing the illuminating beam into an eye of the subject is disposed between the phoropter and the eye of the subject, such that the illuminating beam does not traverse the phoropter before impinging on the eye of the subject.

In such systems, the optical system for directing the illuminating beam into the eye of the subject may have a thickness in the direction of the optical axis of the system such that the phoropter can be positioned no further than a standard distance of spectacle lenses from the eye. Such an optical system for directing the illuminating beam into the eye of the subject may comprise a plate having beam splitting properties over only a central part of its aperture.

Alternative implementations perform a method for measuring properties of the eye of a subject, comprising:
(i) providing a wavefront analyzer for determining the aberrations of a wavefront reflected from the eye of the subject, light from the eye being directed into the wavefront analyzer by means of a focusing system, and
(ii) adjusting the axial position the focusing system such that the beam width of corneal reflected light entering the wavefront analyzer, is adjusted according to the properties of the eye which it is desired to measure. In such a method, the axial position of the focusing system is adjustable to provide a beam of light reflected from the cornea of the eye of width sufficiently large to enable the wavefront of the corneal reflected light to be analyzed by the wavefront analyzer, such that information regarding the corneal profile of the eye can be determined.

Additionally, the axial position of the focusing system may be adjustable such that the corneal reflected light enters the wavefront analyzer as a substantially collimated beam.

Alternatively, the axial position of the focusing system may be adjusted such that the beam of corneal reflected light is focused onto the wavefront analyzer in the central region of the wavefront analyzer. In such a situation, when the axial position of the focusing system is adjusted such that the beam of corneal reflected light is focused onto the wavefront analyzer in the central region of the wavefront analyzer, light reflected from the retinal surface of the eye is arranged to form an essentially collimated beam at the wavefront analyzer, such that the aberrations of the eye can be measured from the deviations of the wavefront. This essentially collimated beam may enter the wavefront analyzer over a substantially larger area of the wavefront analyzer than the central region of the wavefront analyzer, such that the corneal reflected light does not flood out the retinally reflected light entering the wavefront analyzer over the substantially larger area.

In such methods, the wavefront analyzer may be capable of being switched between eye aberration measurements and corneal profile measurements by adjustment of the axial position of the focusing system relative to the position of the eye being measured.

Another example implementation can involve a method for determining aberrations in the eye of a subject by performing a sequential objective wavefront analysis of the residual aberration in the vision of the eye and a subjective phoropter measurement, using the objectively measured aberrations to adjust the settings of the vision correction elements in the subjective phoropter measurement, and repeating the measurements iteratively until the residual aberration is below a predetermined minimum value.

The above described method may comprise at least some of the steps of:
(i) providing a measurement system incorporating:
  (a) a phoropter disposed in front of the eye of the subject, such that the vision of the eye of the subject can be subjectively corrected, and
  (b) a wavefront analyzer for determining objectively the aberrations of the eye of the subject after correction by the phoropter, the wavefront analyzer being disposed such that light emitted from the eye enters the wavefront analyzer after traversing the phoropter,
(ii) performing a first objective measurement of the eye using the wavefront analyzer,
(iii) adjusting the settings of the phoropter to correct the aberrations of the eye as measured by the first objective measurement,
(iv) performing a first subjective correction of the vision of the eye using the phoropter,
(v) performing a second objective measurement of the eye using the wavefront analyzer, to determine the aberrations of the eye after the first subjective correction by the phoropter,
(vi) readjusting the settings of the phoropter to correct the aberrations of the eye as measured by the second objective measurement,
(vii) performing a second subjective correction of the vision of the eye using the phoropter with the readjusted settings, (viii) determining whether the number of iterative steps has exceeded a predetermined number and if so outputting the last phoropter setting as the optimum prescription, (ix) if the number of iterative steps has not exceeded the predetermined number, determining the residual aberration detected at the last objective wavefront analysis, and if less than a predetermined level, outputting the last phoropter setting as the optimum prescription, and (x) if the residual aberration detected at the last objective wavefront analysis is more than the predetermined level, continuing with the iterative objective and subjective measurements.

Finally, although the system has generally been described and often claimed as a binocular system acting on both eyes, as is essential for those implementations involving mutual motion of the phoropters for both eyes such as for measurement of pupil distance, it is to be understood that the disclosure is not intended to be limited to binocular applications, but is equally well intended to apply to each individual eye separately, where appropriate.

BRIEF DESCRIPTION OF THE DRAWINGS

The presently claimed invention will be understood and appreciated more fully from the following detailed description, taken in conjunction with the drawings in which:

FIG. 2 shows the position of the illumination beam in the system of FIG. 1, with the input beam offset from the optical axis of the eye to reduce corneal reflection;

FIG. 3 illustrates the phoropter section of the combined phoropter and wavefront analyzer system of FIG. 1, according to an implementation of the systems described in the present application;

FIG. 4 illustrates a typical Shack Hartmann deflected spot image, as detected on the imaging detector array, with the illuminating beam too close to the optical axis of the eye;

FIG. 5 illustrates schematically a monitor display of the Shack-Hartmann spot array, such as would enable the centering of the measurement channel with the subject's pupil, such that the pupil distance can be measured automatically;

DETAILED DESCRIPTION

Figure 1:
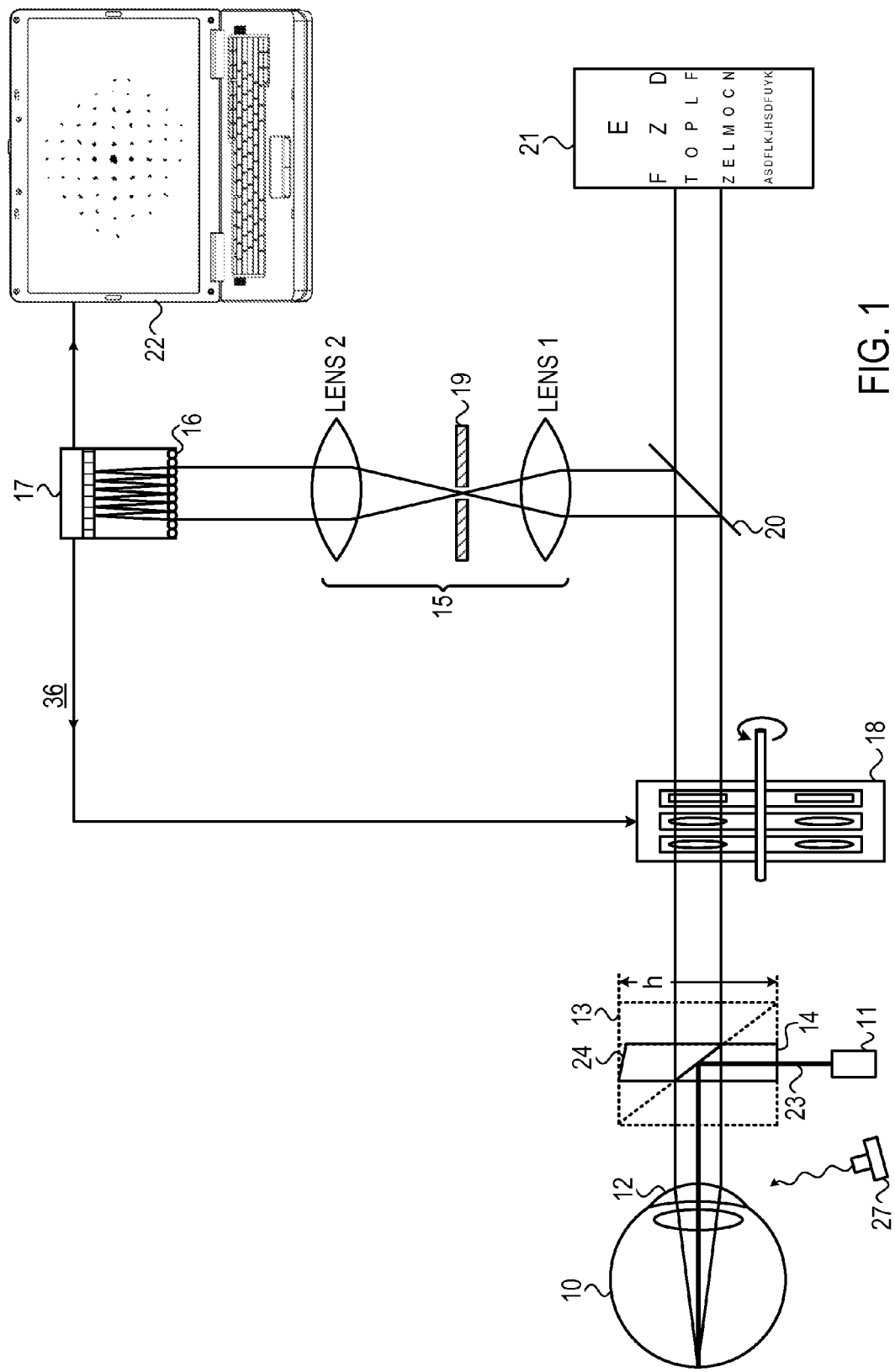
FIG. 1 illustrates schematically an exemplary combined phoropter/wavefront analysis system, as described in the present disclosure.

Reference is now made to FIG. 1, which illustrates schematically an example of a combined phoropter/wavefront analysis system of the type disclosed in this application. The subject's eye 10 is illuminated by means of a laser 11, though any other suitable collimated light source could be used, whose beam is directed into the eye by means of a beam splitter 14 located immediately in front of the subject's eye. The illumination is focused by the eye's optics towards the subject's retina, and the light reflected from the retina passes back through the optics of the eye, back through the input illumination beam splitter 14, and through the lens wheels of a phoropter 18. It may then be directed by a second beam splitter 20, away from the direct line of sight of the subject, and is optically focused through a pinhole beam aperture 19 disposed between a pair 15 of focusing lenses LENS1 and LENS2, and is directed into a Shack-Hartmann (SH) detector array. This most conveniently incorporates a lenslet array 16, which focuses the incident waveform onto the pixelated two-dimensional detector with its signal processing and output electronic circuits 17, from which the refractive map of the eye is extracted. The information can be displayed on the instrument monitor 22, either in digital form, or as an image of the SH spots, or as a refractive map of the eye under test. A Snellen chart 21, or an equivalent target, is disposed in the direct line of sight through the second beam splitter 20, for the subjective aspects of the phoropter measurement by direct vision through this beam splitter 20. It is to be understood, however, that the positions of the Snellen chart and the SH detector could also be exchanged, with the chart being viewed by right angle diverted vision through the beam splitter. However, there are advantages to the arrangement shown in FIG. 1 with the target viewed by direct vision through the beam splitter, as there may be instrument accommodation effects if the viewing is not natural, and one of the advantages of the present instrument is that it avoids such effects which may be present in regular wavefront and other autorefractometer devices.

There are a number of advantages in a system such as that shown in FIG. 1, wherein the laser illumination of the subject's retina is along an optical path free of any refracting, diffracting or phase altering components. A system for wavefront measurement only using this arrangement has been described in U.S. Pat. No. 6,736,509 to R. J. Martino et al, for "Aberrometer Illumination Apparatus and Method", in which there is described a Shack-Hartmann wavefront sensing measurement system in which the laser illumination is steered into the subject's eye by means of a beam splitter positioned immediately in front of the eye. In U.S. Pat. No. 6,736,509, there is described the advantage that the laser beam is not distorted by passage through any other optical components before entry into the eye, such that the illumination beam maintains its Gaussian propagation mode with a tight beam waist and a Rayleigh range that extends over a specified refractive error range. This enables the provision of foveal illumination with a beam diameter that is less than the diffraction limit of the beam through the lenslets that image the wavefront reflected from the retina onto the SH detector over a wide range of aberrations. This enables a more accurate refractive measurement to be made. However, in the present described system, which combines a phoropter measurement with the wavefront measurement, another important advantage exists for this input beam position, since no input laser beam reflections are generated from optical surfaces other than the subject's cornea, such as from the numerous optical surfaces in the phoropter, as will be discussed hereinbelow. Reflections from external optical components could be of an intensity which would flood out the tiny retinal reflection signals which the system is attempting to measure.

However, if it is attempted to apply such an arrangement to a combined phoropter/wavefront analysis instrument, such as that described in the above-referenced International Patent Application Number WO 2005/037090, a conventional cubic beam splitter, as shown by the dotted outline 13 of the beam splitter of FIG. 1, would have a serious disadvantage. In order to cover the entire field of view of the subject, the lateral dimensions (height h and width) of the beam splitter perpendicular to the optical axis should be at least approximately of the same size as the subject's corneal diameter, as shown in FIG. 1, so that the subject does not see the outline of the beam splitter. However in this case, using a conventional beam splitter cube, the necessary path length of the region in which the beam splitter is inserted would also be of the same order of magnitude as the height, h, of the cube, and this would necessitate the positioning of the phoropter elements at a substantial distance from the eye. In order to achieve realistic results with the phoropter, it should be positioned at the same distance from the eye as a pair of spectacle lenses, i.e. approximately 12 mm, and the beam length of a conventional cubic beam splitter with its mounting space would be considerably more than this.

In order to overcome this problem, a novel beam splitter configuration is proposed, specifically optimized for use in the combined phoropter/wavefront analysis instrument of the present disclosure. Part of the cubic beam splitter has been removed, as shown by the dashed outline of the beam splitter 13, in order to generate a low-profile, beam splitter "slice" 14, that has a very short insertion length into the beam path. The narrow laser beam 23 directed into the beam splitter is correctly deflected towards the subject's eye 10, while the light reflected from the subject's retina, which is to be measured, is allowed to fill the entire aperture of the beam splitter. The optical length of the "slice" need be only fractionally more than the diameter of the laser beam 23, which could be of the order of 1 mm. By this means the beam splitter fulfills its purpose but does not require the phoropter elements to be distanced from the subject by more than the desired standard distance of 12 mm. The face 24 of the beam splitter slice 14 opposite the entry face of the laser beam, may advantageously be formed with a wedged surface, so that any reflection of the laser beam striking the far edge 24, will not be directed back to the beam splitter interface and into the measurement system. In addition, it is advisable that the whole beam splitter 14 be mounted with the normal to its faces at a small angle—which can be approximately 3°—from the optical axis, in order to prevent the laser exiting the front surface from being axially reflected and reaching the Shack Hartmann detector.

In order to prevent the subject from seeing a narrow strip of the beam splitting region running across the width of the aperture of the subject's field of view, the reflectivity of the beam splitting coating has to be arranged such that the light level passing through the beam splitting central region is similar to that passing through the rest of the beam splitter slice 14. This can be achieved by using a beam splitting coating having a fairly high transmissivity, and only a small part of the input laser light is deflected into the subject's eye. As an example, if the beam splitting coating is manufactured to have a reflection ratio of only 5%, it will appear to transmit 95% of the incident light. Therefore, the subject looking through the beam splitter will see 95% transmission in the central beam splitting swathe of the beam splitter 14. If the antireflection coating applied over the entire faces of the beam splitter slice 14 is such that it reduces overall reflection from both surfaces to 5%, then there will be virtually no difference in transmission between the central beam splitting section and the rest of the component aperture. Such a beam splitting percentage has the added advantage that it reduces the level of laser light entering the eye making the system more eye safe. An additional eye safety feature is that the low laser beam intensity obviates the need for a protective filter to reduce the intensity of the incident laser light, with the incumbent problems of assuring the integrity and position of that filter.

In order to reduce the level of corneal back reflection from entering the wavefront sensing path, the illumination beam should be positioned so that it enters the eye off-axis, as is known in the art. This is shown in FIG. 2, where the input beam 25 is offset from the optical axis of the eye by distance D, such that the corneal reflected beam 26 is reflected at an angle such that it does not pass through the aperture 19, and is blocked from entering the Shack Hartmann array. A distance D of the order of 1 mm or more, is sufficient to divert the reflected beam at an angle such that it does not enter the Shack Hartmann array. Due to the offset of the illuminating beam, the position of the focused spot on the retina will vary with the refractive condition of the eye being measured. For essentially all eyes, even those with high aberrations, this level of offset does not prevent the illuminating spot from falling well within the fovea of the retina. Thus, as stated in the above referenced U.S. Pat. No. 6,736,509 to R. J. Martino et al, for aberrations of from +6 diopters to −12 diopters, the focal point of an illuminating beam off-axis by 1 mm will be offset from the center of the foveola by distances of from 0.10 mm to −0.21 mm respectively, both of which are well within the fovea. Strong reflections from the cornea are thus prevented from interfering with the detection of the comparatively much weaker light reflected from the retina, essentially without degrading the retinal reflection level.

According to further implementations of the instruments of the present disclosure, as described hereinbelow, the positions of the focusing elements of the instrument can be adjusted to focus the corneal reflection on the lens array in such a manner that the corneal reflection falling on the detector is minimized.

Prevention of the "blinding" of the detector by the corneal reflected light is an important feature in enabling a sensitive detection regime to be achieved in a wavefront analyzer. This is generally performed by lateral or more preferably, by vertical positioning of the illumination beam so that the beam does not enter the pupil on-axis. According to yet another implementation of the present combination instrument, excessive illumination on the wavefront analyzer detector array is used as a warning that the illuminating beam is still too close to the optical axis, and that it should be moved further away from the axis to enable optimum analysis of the deflected SH spots to be obtained. The instrument alignment is set up such that when the SH image is centered using the screen image—this implying that the measurement axis is aligned with the visual axis of the eye—the laser illumination is set to be off-axis by about 1 mm from this coaligned axis, 1 mm typically being approximately the laser beam width. If in this position there is still a disturbing reflection, that is readily noticeable on the screen, typically with a region with larger spots and an increased background level, a control system using a motion system driven by a signal derived from the illumination level falling on the wavefront detector can be used to slightly move the complete measurement and illuminating beam assembly, until the excessive corneal reflection is reduced below a predetermined acceptable level. This motion can be achieved by means of the phoropter pupil distance adjustment motors, as shown in FIG. 3 hereinbelow, using a servo drive signal 36 obtained from the SH image analysis program, as shown in FIG. 1 previously. Although such a motion also moves the measurement axis from collinearity with the eye's optical axis, the required movement is sufficiently small that the measurement is not affected. As an alternative, the feedback signal can be used to move just the position of the illuminating beam, such as can be achieved by laterally moving the beamspiitter slice 14, but the former implementation may be more convenient since the phoropter assemblies are already independently fitted with lateral motion motors in order to adjust and measure the pupil distance, as will now be described hereinbelow.

Reference is now made to FIG. 3, which illustrates part of an exemplary combined phoropter and wavefront analyzer system, according to one implementation of the systems described in the present application. The system of FIG. 3 utilizes two features of the phoropter in order to simplify the procedure of ensuring that the illuminating beam is applied off-axis. In order to adjust the phoropter for use with subjects having different pupil distances, the lens wheel assemblies 30, 31, of the phoropter are equipped with a motion mechanism which enables them to move closer together or further apart, as depicted by the arrow 34 indicating the motion generated by the motion mechanism which itself is not shown in FIG. 3. The motion mechanism operates so that the viewing apertures disposed optically in line with the test lens locations can be spaced apart at a distance equal to the pupil distance.

In addition, the lens wheel assemblies 30, 31, are also equipped with a swivel mechanism that enables their mutual angular alignment relative to the viewing axis to be adjusted. Therefore, whereas for distance vision tests, the phoropter wheels are aligned with their axes parallel, for testing close-up vision, the lens wheels will be tilted inwards, as shown by the dotted outline lines 37, to match the angle at which the subject's eyes are being tilted, in order to accommodate for the close up viewing tests.

The present combination phoropter/aberrometer instrument utilizes the phoropter adjustment features in order to ensure off axis illumination to avoid corneal reflections from disturbing the aberrometric measurement. Thus, if the illuminating beam 33 is too close to the optical axis of the eye 32, either the pd spacing mechanism 34, or the phoropter wheel tilt mechanism 37 can be operated in order to distance the illumination beam from the optical axis of the eye.

Reference is now made to FIG. 4 which illustrates a typical Shack Hartmann deflected spot image, as detected on the imaging detector array. The array of spots 40 is shown for an emmetropic eye such that all of the spots are uniformly arranged. The exemplary array shown in FIG. 4 is obtained from a measurement in which the illuminating beam is too close to the optical axis, and those of the spots close to the position of the beam have a significantly higher intensity than the other spots. These spots are shown in the region 42. In addition, the general background illumination from the corneal reflection may be sufficiently intense that it floods out the spot illumination from the retinal reflection having a much lower level of intensity. Both these effects can be used as a feedback source in order to drive the phoropter pd spacing or tilt motors, in order to bring the spots to a more uniform and to a lower intensity level. This is shown referring back now to FIG. 1, where an output signal 36 from the processing circuitry of the detector output 17 of the Shack Hartmann detector, or from the system data processor, is used as a feedback signal to the lateral motion and/or tilt mechanism of the phoropter wheel assemblies 18, together with their associated focusing and SH analyzing components.

The previously described arrangements for controlling the position and/or tilt of the phoropter wheels have been used for ensuring that the incident laser illumination falls slightly off axis, so that the retinal reflection is not flooded out by the corneal reflection. According to a further implementation of the systems described in this disclosure, a feedback mechanism can be used in order to perform an auto centering procedure, to ensure that the axis of each of the right and left eye measurement assemblies are correctly aligned with the pupils of the subject's eyes—other than the slight offset required to avoid strong corneal reflections, as previously mentioned. (In this section it should be noted that when reference is made to centralized pupil alignment, or similar terms, the intention is for alignment of the center of the pupil, other than that slight offset required to avoid strong corneal reflection.) By use of this arrangement it becomes possible to perform an automatic measurement of the pupil distance of the subject.

Reference is now made to FIG. 5, which shows a typical screen of the SH analyzer monitor, when the center of the subject's pupil of the eye being analyzed is not aligned with the center of the optical axis of the SH analyzer. In the example shown, the SH spot pattern is shown deflected to one side of the monitor screen, reflecting the lateral offset of the pupil from the SH measurement axis. A simple image processing routine can be used to measure the offset of the center of the SH spot pattern from the SH measurement axis, adapted to be at the center of the monitor. The value of this offset can then be used as feedback 36 to the motor controlling the lateral motion of the measurement assembly (including phoropter wheel, focusing optics and SH analyzer array) associated with that eye, in order to bring the pattern to the center of the monitor, indicating that the measurement is being performed with the subject's pupil aligned with the optical axis of the measurement assembly. The feedback mechanism can be operated on the optical "channel" of each eye independently and simultaneously, and a measurement of the motion provided to each of the eye channels from their initial known position enables an automatic measurement of the pupil distance (pd) to be performed. Such a measurement therefore overcomes the problem with current image based pd measurements, where the center of the pupil of each eye is measured sequentially, such that if the subject moves between each measurement, the measurement becomes unreliable. The automatic pd measurement according to the present implementation of the systems of this disclosure should also provide substantially greater precision than similar measurements done visually by the optometrist.

In addition to measuring the pupil distance using lateral motion control and measurement, analysis of the position of the SH pattern on the monitor screen can also be used in order to centralize the measurements in the vertical direction, by using a motion system (not shown in FIG. 1) which adjust the vertical position of the measurement system relative to the subject's eyes, which is generally maintained in a fixed position by use of a fixed head or chin rest.

Furthermore, the pupil diameter of each eye can be measured, by analysis of the image of the SH spots shown on the monitor. This can be done either manually by the user, or automatically using an image processing procedure. The measurement of the pupil diameter is an important additional parameter for use in characterizing the prescription measured using the combined instrument. It is known that the pupil diameter at the time of a subjective phoropter measurement can have an effect on the resulting prescription obtained for that eye, since the level of some aberrations depends on the pupil diameter. The pupil diameter is therefore an additional parameter to be specified when prescribing the lenses required by the subject, and it is feasible that an agreed standard pupil diameter will become a common parameter when specifying a correction lens. In the presently described instrument, the pupil size can be measured automatically by image processing of the Shack Hartmann image of the eye being tested. The pupil diameter is obtained from a measurement of the total size of the spot image on the detector, the spot image arising from the light reflected from the retina which passes out through the pupil. The larger the pupil size, the larger the SH spot image size. During the instrument calibration, the size of the SH spot array image arising from an artificial eye with a known pupil size is measured, this giving a calibration of the SH sensor pixel size in mm units of pupil diameter. Artificial eyes with different eye powers can be calibrated separately to give different calibration values for the change of magnification with eye power. Then for instance, if the pupil diameter needs to be increased or decreased to reach the standard size, the room illumination can be adjusted in order to achieve this result.

Reference is now made to FIGS. 6 to 10, which illustrate schematically the optical arrangement for a further implementation of the present combined phoropter/wavefront analysis instrument, adapted to enable a keratometric measurement to be performed on the central section of the subject's cornea. The corneal reflection spots can be used to measure the corneal radius since the spots change position according to the curvature of the position on the cornea from where the reflections are coming. The measurement uses the Shack-Hartmann array in order to analyze the small deviations in position of the reflections from the cornea resulting from the curvature of the cornea. Since the spot movements resulting from the corneal curvature are small (due to the small differences of the curvature of the cornea from a standard curvature used to define the typical corneal curvature), a high resolution camera is required, typically of the order of 5 or 10 megapixels, in order to be able to accurately plot the small changes in spot position. In order to perform this measurement, two adjustments are necessary to the settings of the instrument used for making the aberration measurements based on analysis of the light from the retinal reflection. Firstly, the axis of the Shack-Hartmann array measurement system must be moved from its off-axis position (which was necessary in order to prevent the corneal reflection from flooding out the much weaker retinal reflection) to the on-axis position in order to receive the light reflected from the cornea. This procedure can be readily carried out using the lateral pd-motion motors to move both of the phoropter wheels and their attached S-H measurement assemblies so that their optical axes are centralized on the optical axes of the eyes. Secondly, the focusing lens assembly must be moved so that the S-H array focuses the light reflected from the corneal surface, rather than the collimated light from the retinal reflection. These two alternative instrument configurations are now further described in FIGS. 6 to 10. which show the outer envelope of the beams reflected from the eye, and are based on ray plot outputs obtained from the Zemax® optical design program for the various configurations to be described.

Figure 6:
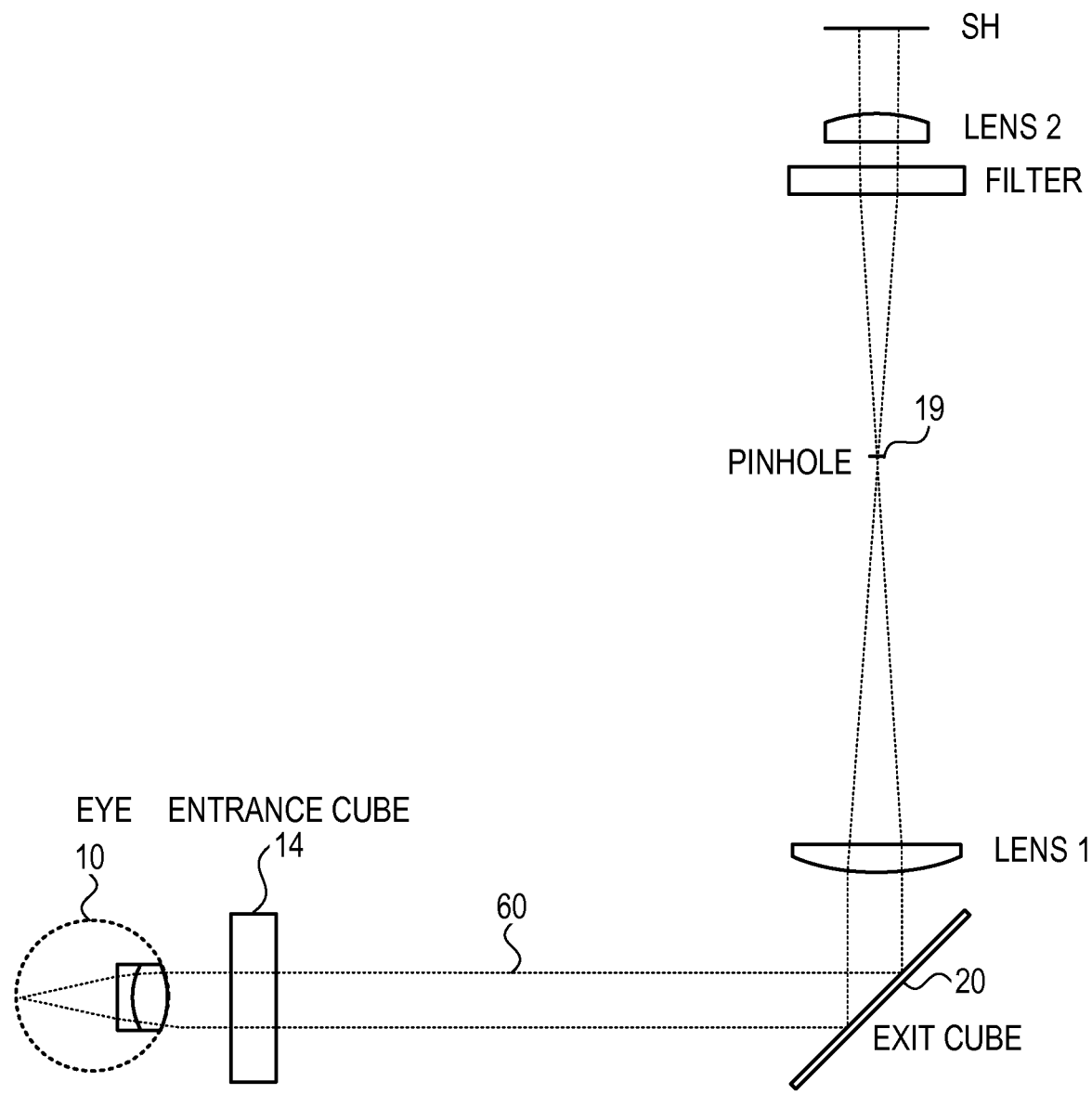
FIGS. 6 to 10 illustrate schematically the optical arrangements to enable a keratomic measurement to be performed on the combined phoropter/wavefront analysis instrument of FIG. 1.

Reference is first made to FIG. 6, which shows a plot for the optical setup for a conventional wavefront analysis measurement for determining the aberrations of a subject's eye 10. The measurement laser beam, input through the beam splitter 14, is focused by the eye's optics towards the retina, and the ray plot of FIG. 6 shows the light reflected from the retina being transformed by the eye's optics to a collimated beam, 60. As described in FIG. 1, this collimated beam is focused by the lens assembly, labeled LENS1 and LENS2 in these figures, through the pinhole 19, and onto the Shack-Hartmann array and camera, shown as a single imaging plane SH in these simplified drawings derived from ray tracing drawings. The filter shown is a long pass filter allowing the generally used near infra red (typically 780 nm) laser illumination to pass while blocking out any extraneous illumination from the room. Because of the collimated nature of the beam being measured, it impinges on much of the full width of the Shack-Hartmann array, and analysis of the movement of the spots from a uniform array, as would be obtained from a plane wave, enables the aberrations of the eye to be determined. It is important to note that because of the collimated nature of the beam entering and leaving the focusing assembly, the wavefront measurement is essentially independent of the position of this focusing assembly (marked 15 in FIG. 1), so long as the lenses LENS 1 and LENS2 and the pinhole 19 are moved in unison.

Figure 7:
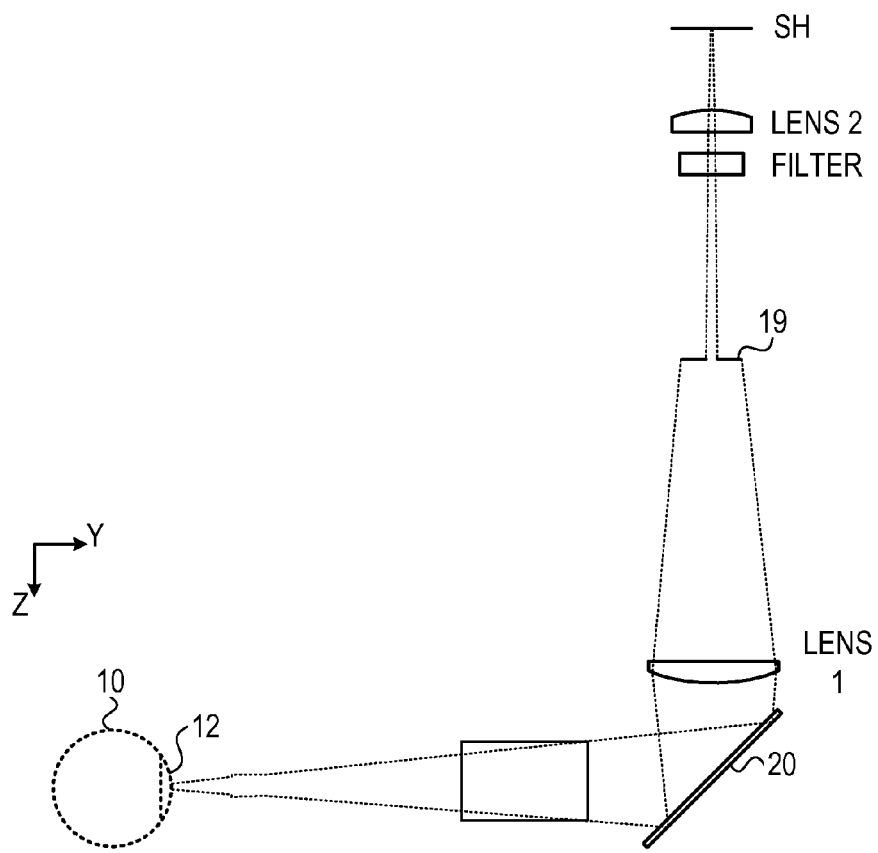
Figure 8:
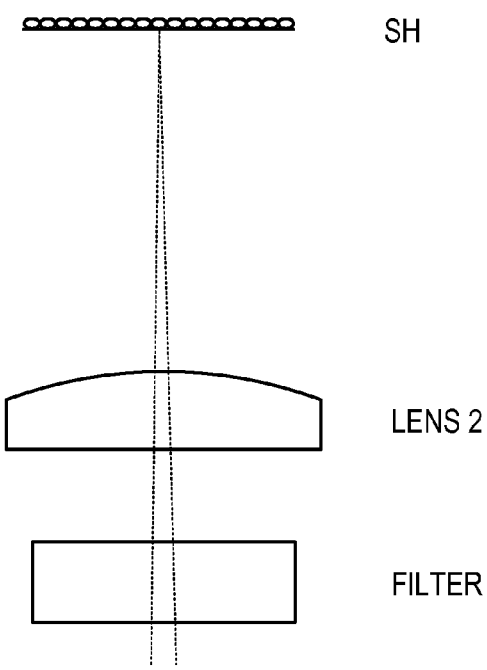

Reference is now made to FIG. 7, which illustrates schematically the path of rays of the laser illumination reflected from the cornea 12 of the subject's eye, when the system is set up, as in FIG. 6, to perform a wavefront analysis of the light reflected from the retina. The laser light is reflected from the front surface of the cornea 12 from a region approximately equal to the width of the laser beam, which could be of the order of 1 mm or so. Because of the convex curved nature of the front surface of the cornea, the parallel incident laser rays are reflected in a divergent beam towards the focusing assembly. As mentioned in connection with FIG. 6, the position of this focusing assembly does not affect the imaging of the retinal reflection wavefront. Therefore, the focusing assembly can be positioned in such a location that it refocuses the diverging corneal reflection rays back into a convergent beam, focused exactly onto the Shack-Hartmann imaging array SH. As seen in FIG. 7, this configuration has two advantageous effects. Firstly, the majority of the beam converging from LENS1 is blocked at the pinhole aperture plane 19, and only a small axial central part of the beam passes through the pinhole. Secondly, because of the selected location of the focusing assembly, that small axial central part of the beam is focused tightly on to the central lenslet (or a few central lenslets) of the Shack-Hartmann array, such that there is little interference with the wavefront measurement over the majority of the SH array. The central spot or central few spots may be overcome by the corneal reflection spots, but the majority of the spot pattern remains clearly distinguishable. FIG. 8 is a zoomed-in section of the ray pattern of FIG. 7, of the final focusing lens LENS2, and the SH focal plane, showing how the central rays of the corneal reflected light can be focused down to no more than an area covering the central single lenslet of the SH array.

This configuration is therefore useful in enabling the system to perform a retinal reflection wavefront analysis, even from an exactly on-axis position, while at the same time preventing the strong corneal reflection from interfering with the retinal reflection measurement.

Figure 9:
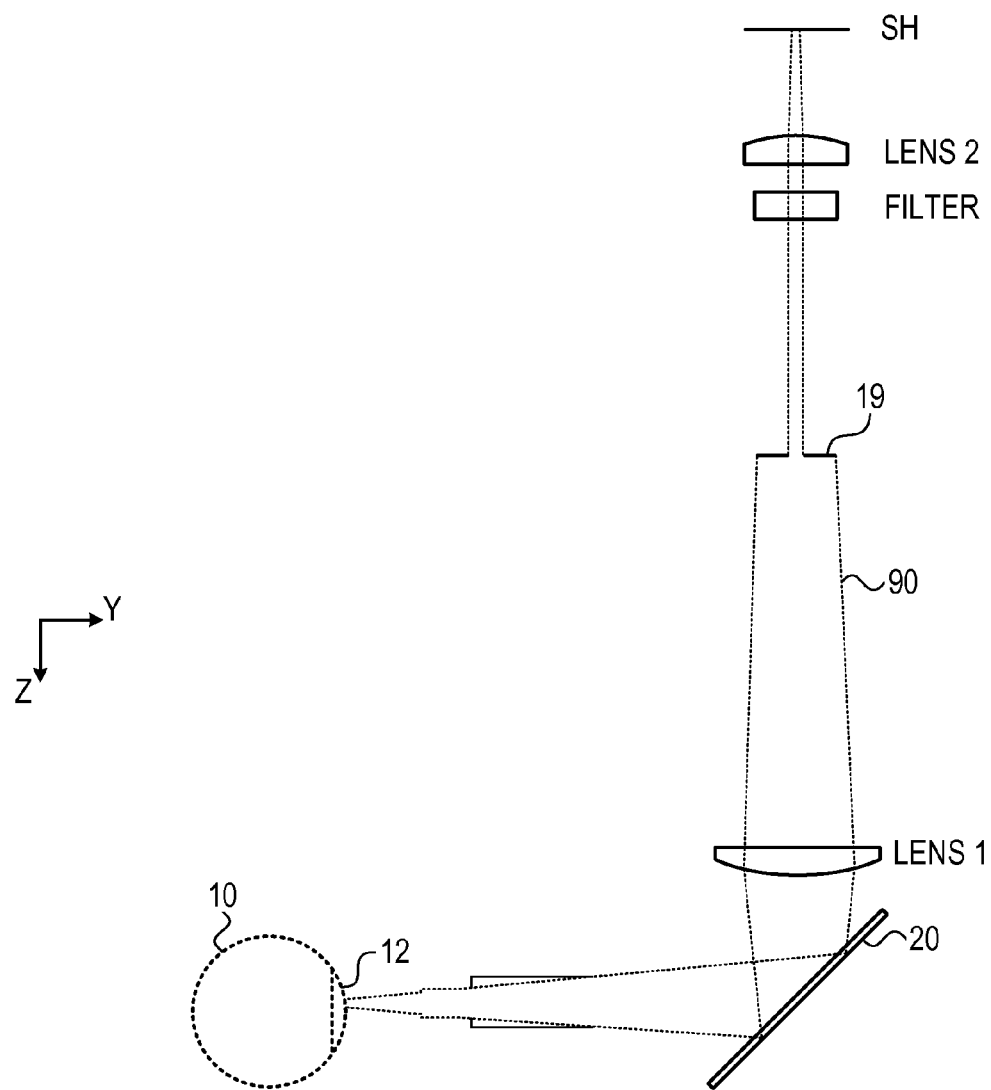

Reference is now made to FIG. 9, which illustrates schematically the path of rays of the laser illumination reflected from the cornea 12 of the subject's eye 10, when the system is set up to use the SH array to perform a keratometry measurement on the central region of the cornea, utilizing the light reflected from the cornea. In order to perform this measurement, the focusing assembly is moved away from the position shown in FIGS. 7 and 8, in which it focuses the corneal reflected light as tightly as possible onto the Shack-Hartmann focal plane SH, and instead attempts to provide a quasi-collimated beam from the corneal reflected light. This can be performed by moving the focusing assembly closer to the subject's eye or further away (though movement closer has the advantages of a more compact instrument), so that the diverging corneal reflection rays are close to being collimated. In FIG. 9, this has been achieved conveniently by moving the entire Shack-Hartmann detection arm of the optical system, including the beam splitter 20, focusing lenses, pinhole 19, and SH detector assembly together, towards the plane of the subject's eye (to the left in the sense of the geometry of FIG. 9). However it is to be understood that any other motion configuration generating a quasi-collimated beam 90, such as by moving just the focusing lenses and SH detector assemblies towards or away from the beam splitter 20 (vertically in the sense of the geometry of FIG. 9), will also achieve the same result. A major part of the collimated beam 90 of the corneal reflection is blocked by the pinhole aperture 19, but the central part of the beam passes through the pinhole and is focused by a LENS2 onto the SH focal plane in a close to collimated beam. The SH detector assembly then provides a spot pattern, with the position of the spots being determined by the curvature of the cornea in its central region. Analysis of the shift of the spots from the regular rectilinear array expected from a planar wavefront, or from the pattern expected from a predetermined uniform curvature, enables a keratometric measurement of the axial region of the cornea to be performed.

Figure 10:
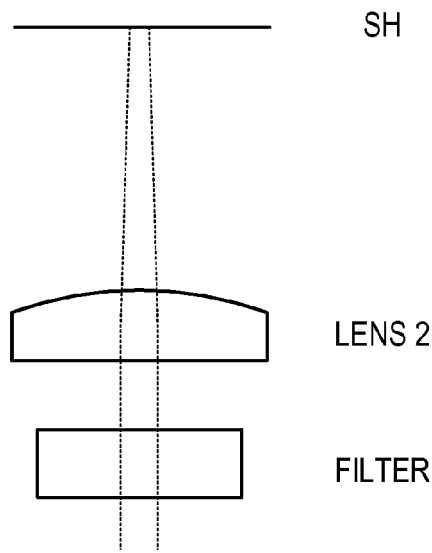

FIG. 10 is a zoomed-in section of the ray pattern of FIG. 9, of the final focusing lens LENS2, and the SH focal plane, showing how the central rays of the corneal reflected light cover the entire central region of the SH array, enabling the system to perform a corneal reflection wavefront analysis, from which the corneal profile can be determined. The measurement is only a keratometer measurement over the central part of the cornea, and not a full corneal topography measurement as only the center of the cornea is used to provide the reflection. This has an advantage over a prior art typical Placido disk corneal topographer or a ring light keratometer, where the central region of the cornea cannot be measured, as there is generally no illumination and hence no reflection from the central region. The presently described system, on the other hand, measures the central region only.

When the focusing assembly is adjusted for measuring the corneal profile, as shown in FIGS. 9 and 10, since the relative position of the lenses in the focusing lens assembly provide an essentially collimated beam from the retinal reflection from the eye, the system can be readily switched to perform retinal wavefront measurements by simply moving the measurement system so that the illumination is slightly off axis relative to the cornea axis. The corneal reflection will then essentially disappear, leaving the collimated retinal reflection beam, which is still correctly focused through the pinhole and back into a collimated beam falling on the SH detector assembly, to measure the retinal wavefront deviation.

Switching between corneal reflection and retinal reflection measurements can thus be simply performed by either of two methods:
(i) by slight lateral motion of the wavefront measurement system or its illumination input, when set up for corneal reflection analysis, such as by using the phoropter motion motors, to prevent the corneal reflection from overpowering the retinal reflection, or
(ii) by axial change of the working distance of the focusing lens assembly (whether or not that motion includes the wavefront measurement beam splitter), such that the corneal reflection is focused into the center of the wavefront measurement system, and does not therefore interfere substantially with the retinal reflection analysis.

Figure 11:
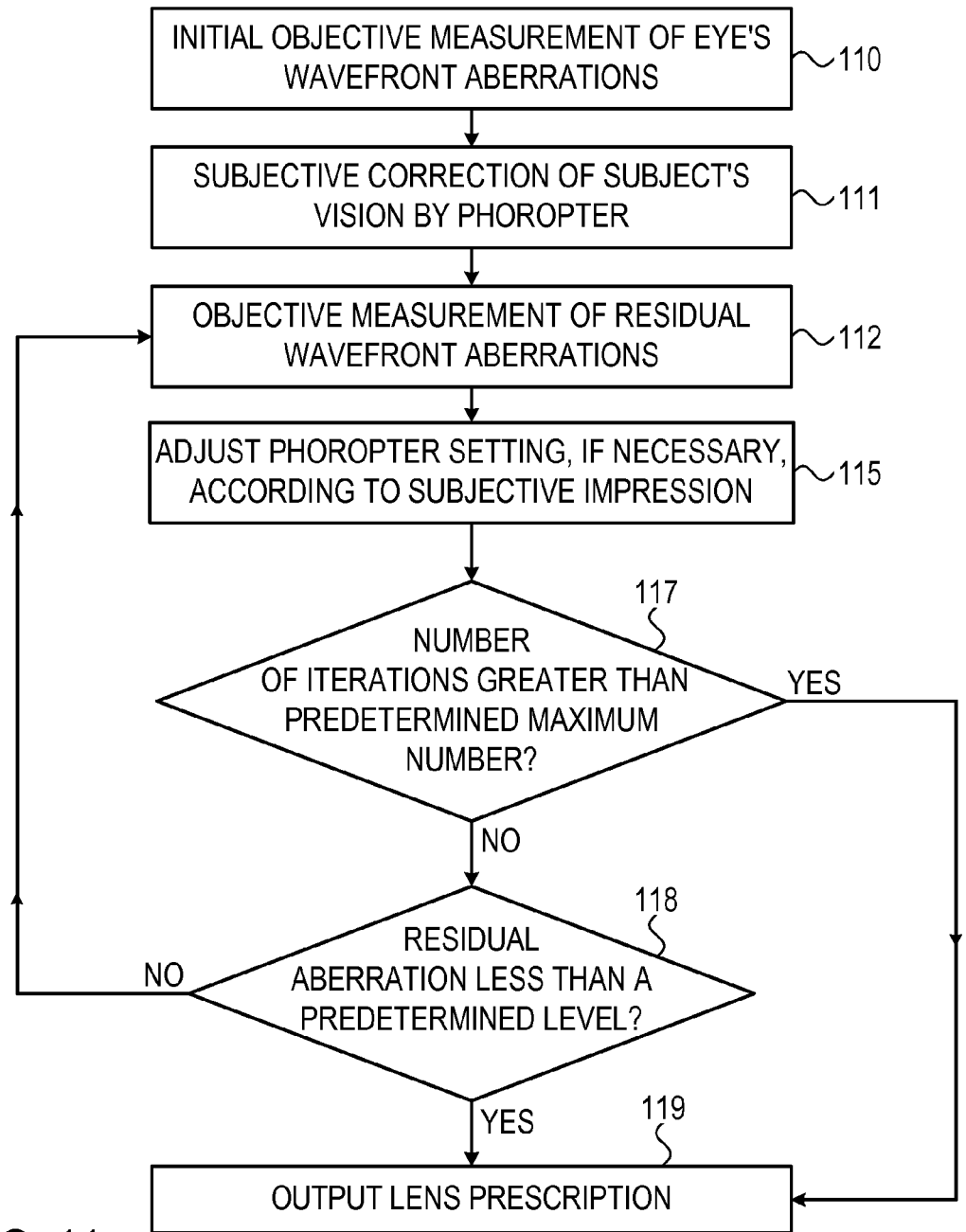
FIG. 11 illustrates a flow chart of a method enabling the subjective phoropter measurement to be iteratively combined with the objective wavefront analysis in order to achieve a more accurate lens prescription for the subject.

Reference is now made to FIG. 11, which illustrates a flow chart of a novel method which enables the subjective phoropter measurement to be iteratively combined with the objective wavefront analysis in order to achieve a more accurate prescription for the subject. Prior art methods combine the subjective phoropter measurement with an objective residual refractometer measurement by using the residual refractive measurement to define the higher order aberrations to be added to the lower order aberrations—sphere, astigmatism and prism—as assessed by the subjective phoropter measurement. This is meant to generate a more accurate prescription for the subject than that which can be obtained with the subjective phoropter measurement alone. Although this does correct for errors generated by the subject's inability to accurately converge on the best prescription based on the low order aberration correction alone, it does not take into account any true subjective effects resulting from the combining of the higher order aberration corrections with the lower order corrections, and the subject may only have the opportunity to experience this once the lenses have been made according to the supposed prescription.

According to the novel methods of the present disclosure, the higher order objective residual aberration measurements are used to provide a further fine correction to the phoropter settings. These settings are generally limited to sphere, cylinder and axis corrections, and there exist methods in the art, such as those described in U.S. Pat. No. 7,357,509 to D. R. Williams et al, for "Metrics to Predict Subjective Impact of Eye's Wave Aberration", of using measured higher order aberrations to give a better value of sphere, cylinder and axis. This particular lens combination is then presented to the subject using the phoropter, so that he/she can confirm that the additional objective refractive measurement has indeed improved his/her subjective feelings about the correction to his/her vision. This iterative process can be repeated more than once, so that the readjusted prescription can more accurately provide vision correction to the subject, including for high order aberrations. In the above referenced patent, a measurement is made of the lower and higher order aberrations, and a calculation is then performed that takes account of both of these measurements to find the best prescription. In the present disclosure, on the other hand, iterative measurements, alternately subjective and objective, are done to try to reduce the residual aberration, rather than the calculations described in the Williams patent.

Referring now to FIG. 11, in step 110, an objective measurement of the wavefront aberrations is performed on one of the subject's eyes, in order to provide starting parameters for use in the initial phoropter settings for that eye. An initial subjective phoropter measurement is then performed in step 111, though this step could also be used as the first step of the method, dispensing with the initial wavefront aberration measurement of step 110. In step 112, an objective measurement is performed of the residual wavefront aberrations remaining after the initial subjective phoropter lens correction of the lower order aberrations, resulting in a new phoropter lens configuration that takes account of the objective measurement performed in step 112. The phoropter wheels are then moved to the new measured lens configuration. For instance, if the objective test 112 gave values of 5D sphere, −2D cylinder at 45 degree axis, those are the values to which the phoropter wheels will be moved at the conclusion of step 112. Then in step 115, further fine adjustments can then be performed to the phoropter setting, to obtain further improvement in the subjective impression of the subject's vision correction. In step 117, a check is performed on the number of iterative loops that the measurement procedure has already done, in order to prevent an infinite loop from being generated if the results do not converge. This will be explained below, after the iterative process has been clarified. In step 118, the total residual wavefront deformation obtained in the last objective measurement after step 115 (whether that of step 115 or a subsequent objective measurement) is compared with a predetermined level, representing a level at which the vision correction is assumed to be optimal, and any further improvement to be of negligible relevance. If this predetermined level has been achieved, the prescription as registered on the last phoropter setting is assumed to be optimal, and the result is output at step 118 for lens manufacture. If the residual aberration level is still above the predetermined threshold, then the method returns to step 112 for a further iterative round of phoropter adjustment and residual aberration measurement, until a result below the threshold is achieved in step 118.

Since it is possible that there may be no end to the iterative loop, and that the objective and subjective measurements are different and non-converging, the counter denoted by step 117 has been inserted into the flowchart steps, so that the loop can be ended after a certain number of predetermined iterations. If the loop is thus terminated, the optometrist will then have to rely on his/her knowledge and experience together with both sets of measurements to decide on the best lens prescription.

Wavefront measurements are generally performed in darkened conditions and the wavefront can be calculated for the entire pupil or for a small part of the pupil to simulate different illumination conditions. For example, if the pupil has a diameter of 7 mm during the measurement, results can be calculated for 3 mm, 5 mm and 7 mm pupils, for example, to simulate different ambient lighting conditions. The subjective test, on the other hand, is generally performed with fixed lighting conditions in the room. The use of the combination subjective/objective instrument of the present application enables the results of both objective and subjective measurements to be brought to the same conditions, such that direct comparison and interactive iterative use of both of the measurements becomes possible.

There exists a problem of how to align the eye of a subject along the optical axis of any ophthalmic measurement system. In conventional objective wavefront analysis systems, such as that described in international Patent Application No. WO2009/024981 for Multifunctional Ophthalmic Measurement System, to the applicant of the present disclosure, a separate imaging camera, boresighted to the wavefront analysis camera, is used in order to obtain a visual image of the subject's pupil, In that application there is described a method in which the subject's eye is imaged on the visual camera, and the image obtained is used to determine when the center of the dark region of the image, which arises from the pupil, is aligned in the center of the camera axis, using the system motor control to reach this central alignment.

However, in the combination phoropter/wavefront analysis systems of the present disclosure, no visual camera is provided. Therefore an alternative method must be found in order to line up the subject's eye with the Shack Hartman camera. According to a further implementation of the methods of the present disclosure, there is described a method in which the subject's eye is dark field illuminated, such as by using an array of infra-red LEDs 27 disposed on the side of the eye, as shown schematically in FIG. 1. Under these conditions, the Shack-Hartmann camera image shows a rudimentary representation of the actual visual field imaged by the SH array. It is presumed that use of the dark field illumination on the side of the eye results in scattered light, and that directed along the axis of the SH imaging system, generates an SH pattern of spots modulated by the contrast of the source plane from which the scattered light originates. Thus, it is believed that the light scattered from the pupil region of the eye is minimal, such that in the SH image, the pupil region appears dark, while the iris region around the pupil scatters a significant quantity of the dark field directed incident light. The SH spot array can then be analyzed in order to determine where the center of the pupil is in the SH camera system, and the SH imaging system can then be moved, by means of the position control system until the center of the pupil is aligned with the axis of the SH array. By this means it becomes possible to align the subject's eye with the axis of the SH camera, without the need for an additional visual camera.

Figure 12:
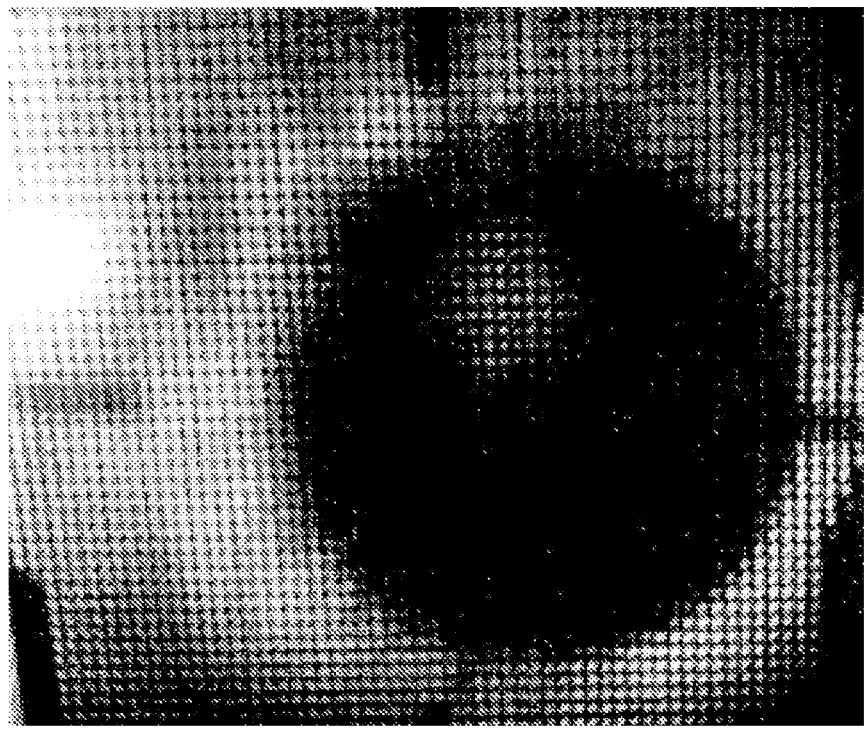
FIG. 12 shows a screen output of a Shack-Hartmann image of a subject's eye generated using the system described in FIG. 1 using dark field illumination for the pupil search.

Reference is now made to FIG. 12, which is an actual screen shot of the Shack Hartmann spot array, taken during such an eye alignment procedure. In the light peripheral regions, the ordered array of Shack Hartmann spots, coming from light scattered from the subject's iris is clearly seen. The central area of the screen is mostly dark since the pupil area scatters very little light, though faint array spots can be seen in some parts of the pupil SH image. If the eye is too far off axis of the SH array, no SH spots are readily visible. However as soon as the iris/pupil interface region is discerned, image processing of the SH spot array image then enables the pupil region to be brought to the center of the screen, which means that the SH camera is aligned axially with the center of the subject's eye. This alignment can be done either by means of a computerized feedback system, or manually by the optometrist or the physician.

An alternative method for determining when the subject's eye is aligned with the SH camera array is proposed using a broader laser illumination beam that is conventionally understood necessary for such measurements. In conventional wavefront analysis systems, and, as described hereinabove, a narrow illumination laser beam is used, typically of the order of 1 mm in diameter. This use of such a narrow beam ensures that the direct corneal reflection of the laser beam is essentially eliminated when working at a sufficiently small distance off axis to ensure that the focused laser beam still falls within the fovea region of the retina. However, according to the present method, use is purposely made of a significantly larger diameter laser illuminating beam in order to determine where the corneal axis relative to the SH imaging camera axis. Such a larger diameter beam covers the center of the cornea as well as off axis regions. As a result, the SH array image shows a very strong spot pattern corresponding to the central axial reflection from the cornea, and much weaker spots in those parts imaging the light coming from off axis regions of the cornea. So long as this strong spot pattern is visible somewhere in the SH image, it can be moved to the center of the SH image by mechanical movement of the SH camera axis, and when centered, it is known that the SH camera axis is correctly aligned with the eye of the subject. The centering can be done either manually by the optometrist, or by means of a feedback circuit operating on the output of image processing of the spot array.

Once the SH camera has been lined up with the optical axis of the eye, the illuminating beam can be switched back to its conventional narrow beam, and moved slightly off axis in order to prevent the strong corneal reflection from flooding out the weak retinal reflection. Switching between the wide centering beam and the narrow wavefront measurement beam can be performed by any conventional known optical technique, such as the use of a telescope or a diverging lens moved along the axis of the input laser beam, or by using a stop, which can be inserted into the beam to reduce its diameter.

Unlike conventional trial frame phoropters which move with movement of the subject's head and are therefore always correctly aligned, digital phoropters are mounted in the instrument and do not move with the subject's head movements. A further method of ensuring alignment of the subject's eye with the SH camera axis utilizes a pinhole element mounted in one of the positions of the phoropter lens wheels. Many digital phoropters include such a pinhole element. In the conventional preliminary alignment procedure, in order to roughly align the subject's eye, he/she is asked to look for the alignment laser beam, known as the "red spot", but this is dependent on the ability and co-operation of the subject, and is therefore susceptible to error. According to the present method, the phoropter wheel is adjusted to insert the pinhole into the optical path, and the subject is asked to look for the Snellen chart through the pinhole by slight movement of his head until the chart is centered in the pinhole. By performing this action, the subject thus, moves his eye to be coincident with the optical axis of the phoropter, which will also be aligned with the optical axis of the Shack Hartmann camera system, thus ensuring accurate positioning of the subject's eye relative to the SH axis. Once this alignment has been performed, the pinhole can be rotated away, following which the objective wavefront measurement and the subjective phoropter measurement, or their iterative combination can be performed in the usual way.

Finally, it should be noted that both the subjective and objective tests may be performed for both monocular and binocular viewing. This is generally done for subjective tests, but at present, is not done for objective wavefront aberration tests. The use of a binocular arrangement in the combination instruments of the present disclosure has a number of additional advantages, besides the inherent advantage of being able to measure both eyes in one set-up, and the ability to measure the pupil distance automatically. As previously mentioned, there is generally a lack of mechanical fixation (such as a chin rest) between the subject's eye and the phoropter wheel. This can lead to cylinder axis measurement error, since the subject can tilt his/her head during the test, such that the line between his eyes is no longer aligned horizontally, while the line connecting the two phoropters is generally horizontal. Using the binocular configuration of the present described instruments, it is possible to compensate for such head tilt by observing the spot array patterns of the SH sensors for the subject's two eyes. If the subject's head is aligned horizontally, both patterns have the same angular alignment. If the two SH sensors show arrays of spots at different heights, that is a sign that the subject's head is tilted, and roll adjustment of the phoropter wheels can be performed until the SH patterns are both symmetrical.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A system for measuring the refractive properties of the eyes of a subject, said system comprising:
    an optical system for directing illuminating beams into the eyes of the subject;
    a phoropter comprising separate phoropter assemblies disposed in front of each of the eyes of the subject, such that the vision of each of the eyes of the subject can be subjectively corrected;
    at least one of a lateral adjustment mechanism for the phoropter assemblies, or an angular adjustment mechanism for the angular alignment between the phoropter assemblies for each of the eyes of said subject, and
    a wavefront analyzer for determining the aberrations of each of the eyes of the subject, said wavefront analyzers being disposed such that light emitted from each of said eyes enters their associated wavefront analyzers after traversing their associated phoropter assemblies,
    wherein at least one of said phoropter adjustment mechanisms is configured to direct said illuminating beams into the eyes of the subject along beam paths not coincident with the optical axes of the eyes of the subject.

2. A system according to claim 1 wherein said lateral adjustment mechanism for the phoropter assemblies is adapted to measure the subject's pupil distance.

3. A system according to claim 2 wherein said lateral adjustment mechanism is controlled by determining the center of the subject's pupils from the intensity distribution of an output image obtained on a detector array of said wavefront analyzer.

4. A system according to claim 1, further comprising illumination sources disposed laterally to said eyes, illuminating the surfaces of said eyes in a dark field mode, such that the wavefront analyzers generate images including arrays of spots from said dark field illumination scattered from the front surfaces of said eyes.

5. A system according to claim 4, wherein said images depict the position of the pupils of said eyes as regions with substantially less illumination than the rest of said images.

6. A system according to claim 1, further comprising focusing assemblies directing light from said eyes into said wavefront analyzers, wherein said focusing assemblies and wavefront analyzers may be disposed on the axis of said eyes, light reflected from the corneal surfaces of said eyes being focused onto the central region of said wavefront analyzers, such that said corneal reflected light does not flood out light reflected from the retinae of said eyes impinging on more peripheral regions of said wavefront analyzer.

7. A system according to claim 6, wherein said focusing assemblies are such that said light reflected from the retinae of said eyes is directed into said wavefront analyzers in essentially collimated beams, such that said collimated beams cover an appreciable area of said wavefront analyzers peripheral to said central region of said wavefront analyzers.

8. A system according to claim 1, wherein said beam paths not coincident with the optical axes of the eyes of the subject are sufficiently far from said optical axes that corneal reflections into said wavefront analyzers are essentially eliminated while the focused beams still impinge on the retinae of said eyes.

9. A system according to claim 8 wherein said illuminating beams are sufficiently small that said beam paths are disposed sufficiently far from said optical axes.

10. A system according to claim 9, wherein said system can increase the size of said illuminating beams to enable said increased-size beams to determine the positions of said optical axes of said eyes relative to the axes of said wavefront analyzers.

11. A method for determining aberrations in the eye of a subject, comprising:
(a) providing a measurement system incorporating:
a phoropter disposed in front of the eye of the subject, such that the vision of the eye of the subject can be subjectively corrected; and
a wavefront analyzer for determining objectively the aberrations of the eye of the subject after correction by said phoropter, said wavefront analyzer being disposed such that light emitted from said eye enters said wavefront analyzer after traversing said phoropter;
(b) performing a first subjective correction of the vision of said eye using said phoropter;
(c) performing a first objective measurement of said eye using said wavefront analyzer, to determine the aberrations of said eye after said first subjective correction by said phoropter;
(d) readjusting the settings of said phoropter to correct the aberrations of said eye as measured by said first objective measurement;
(e) performing a second subjective correction of the vision of said eye using said phoropter with said readjusted settings; and
(f) determining the residual aberration detected at said first objective measurement of said eye using said wavefront analyzer, and
(i) if less than a predetermined level, outputting the phoropter setting of said second subjective correction as the optimum prescription, and
(ii) if more than said predetermined level, performing an iteration of a further objective measurement using said wavefront analyzer and a further subjective correction using said phoropter after readjusting the settings of the phoropter to correct the residual aberrations measured by said further objective measurement, according to steps (c) to (e).

12. A method according to claim 11, comprising the further step of determining whether the number of said iterations of further objective measurements and further subjective corrections of said eye has exceeded a predetermined number, and if so outputting the last phoropter setting as the optimum prescription.

13. A method according to claim 11, comprising the further steps of:
performing a preliminary objective measurement of said eye using said wavefront analyzer; and
adjusting the initial settings of said phoropter to correct the aberrations of said eye as measured by said preliminary objective measurement.

14. A method for determining aberrations in the eye of a subject comprising:
providing a measurement system incorporating:
a phoropter disposed in front of the eye of the subject, such that the vision of the eye of the subject can be subjectively corrected; and
a wavefront analyzer for determining objectively the aberrations of the eye of the subject, said wavefront analyzer being disposed such that light emitted from said eye enters said wavefront analyzer after traversing said phoropter;
performing an objective wavefront measurement of the aberration in the vision of the eye using said wavefront analyzer;
subsequently performing a subjective phoropter measurement, using the objectively measured aberrations to adjust the settings of vision correction elements in the subjective phoropter measurement; and
repeating said objective and subjective measurements iteratively until the objectively measured residual aberration falls below a predetermined minimum value.

* * * * *